(12) United States Patent
Ramirez et al.

(10) Patent No.: US 10,952,752 B2
(45) Date of Patent: Mar. 23, 2021

(54) POSTERIOR CERVICAL FIXATION SYSTEM

(71) Applicant: SPINE WAVE, INC., Shelton, CT (US)

(72) Inventors: Pedro Ramirez, Orlando, FL (US); Zachary Gregory, St. Louis, MO (US)

(73) Assignee: SPINE WAVE, INC., Shelton, CT (US)

( * ) Notice: Subject to any disclaimer, the term of this patent is extended or adjusted under 35 U.S.C. 154(b) by 0 days.

(21) Appl. No.: 16/787,111

(22) Filed: Feb. 11, 2020

(65) Prior Publication Data

US 2020/0253621 A1    Aug. 13, 2020

Related U.S. Application Data

(60) Provisional application No. 62/804,941, filed on Feb. 13, 2019.

(51) Int. Cl.
| | |
|---|---|
| *A61B 17/16* | (2006.01) |
| *A61B 17/02* | (2006.01) |
| *A61B 17/17* | (2006.01) |
| *A61B 17/70* | (2006.01) |

(52) U.S. Cl.
CPC ........ *A61B 17/1757* (2013.01); *A61B 17/025* (2013.01); *A61B 17/1671* (2013.01); *A61B 17/7064* (2013.01); *A61B 2017/0256* (2013.01)

(58) Field of Classification Search
CPC .............. A61B 17/1671; A61B 17/025; A61B 17/1757; A61B 17/7064; A61B 2017/0256
See application file for complete search history.

(56) References Cited

U.S. PATENT DOCUMENTS

| | | | |
|---|---|---|---|
| 7,699,878 B2 | 4/2010 | Pavlov et al. | |
| 7,708,761 B2 | 5/2010 | Petersen | |
| 7,837,713 B2 | 11/2010 | Petersen | |
| 7,846,184 B2 | 12/2010 | Sasso et al. | |
| 7,981,114 B2 * | 7/2011 | Zander ................... | A61B 17/17 606/80 |
| 8,267,966 B2 | 9/2012 | McCormack et al. | |
| 8,361,152 B2 | 1/2013 | McCormack et al. | |
| 8,425,558 B2 | 4/2013 | McCormack et al. | |
| 8,753,345 B2 | 6/2014 | McCormack et al. | |
| 9,119,645 B2 | 9/2015 | McBride | |

(Continued)

*Primary Examiner* — Christian A Sevilla
(74) *Attorney, Agent, or Firm* — Hoffmann & Baron, LLP

(57) ABSTRACT

A posterior cervical fixation system includes a facet lock comprising an elongate member having distal and proximal ends. A tapered wedge projects axially from the distal end and defines a wedge axis, the wedge being sized and configured for insertion into a facet joint of a cervical spine. The facet lock includes opposing first and second dovetail recesses. The system further includes a tubular guide having distal and proximal ends and a lumen extending therethrough along a central axis. The tubular guide has a plurality of dovetail projections extending exteriorly outwardly, each dovetail projection terminating in an engagement surface that is spaced respectively at a different radial distance from the central axis. Each dovetail projection is configured for individual releasable attachment to one of the facet lock first or second dovetail recesses to selectively space the wedge axis and the central axis at different distances for lateral mass screw placement.

20 Claims, 16 Drawing Sheets

(56) References Cited

U.S. PATENT DOCUMENTS

| | | | |
|---|---|---|---|
| 9,622,791 B2 | 4/2017 | McCormack et al. | |
| 9,924,972 B2 | 3/2018 | Yue | |
| 2002/0068941 A1* | 6/2002 | Hanson | A61B 17/1757 606/79 |
| 2005/0137601 A1* | 6/2005 | Assell | A61B 17/1671 606/79 |
| 2005/0288677 A1* | 12/2005 | Stauber | A61B 17/8866 606/90 |
| 2006/0241597 A1 | 10/2006 | Mitchell et al. | |
| 2009/0216238 A1* | 8/2009 | Stark | A61F 2/30988 606/96 |
| 2009/0270929 A1 | 10/2009 | Suddaby | |
| 2009/0306671 A1* | 12/2009 | McCormack | A61B 17/025 606/90 |
| 2009/0312763 A1* | 12/2009 | McCormack | A61B 17/8822 606/83 |
| 2010/0004657 A1* | 1/2010 | Dudasik | A61B 17/1757 606/96 |
| 2010/0331883 A1* | 12/2010 | Schmitz | A61B 17/1604 606/249 |
| 2011/0190821 A1 | 8/2011 | Chin | |
| 2014/0276848 A1* | 9/2014 | Leguidleguid | A61B 17/1671 606/83 |
| 2015/0272593 A1* | 10/2015 | Anderson | A61B 17/14 623/17.11 |
| 2015/0342648 A1 | 12/2015 | McCormack et al. | |
| 2017/0071588 A1* | 3/2017 | Choi | A61M 29/00 |
| 2018/0333277 A1* | 11/2018 | Finkel | A61B 17/1671 |
| 2019/0247099 A1 | 8/2019 | McCormack et al. | |
| 2020/0253619 A1* | 8/2020 | Gregory | A61B 17/1757 |
| 2020/0360155 A1* | 11/2020 | Abdou | A61F 2/4601 |

\* cited by examiner

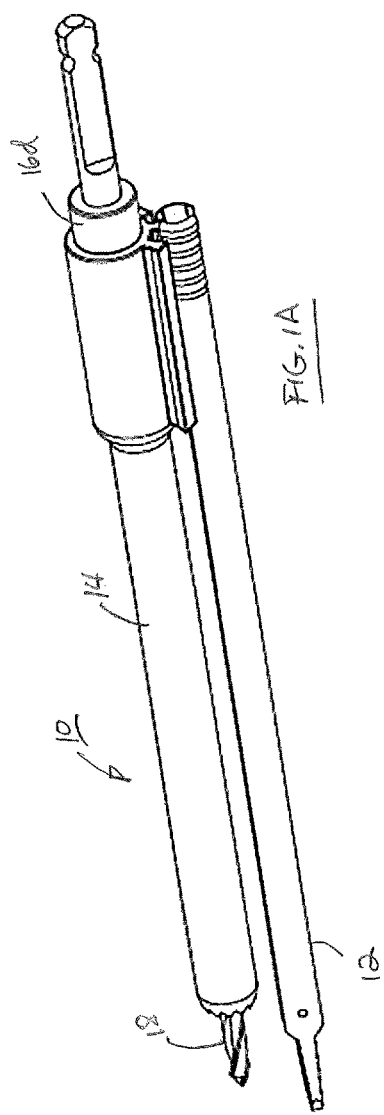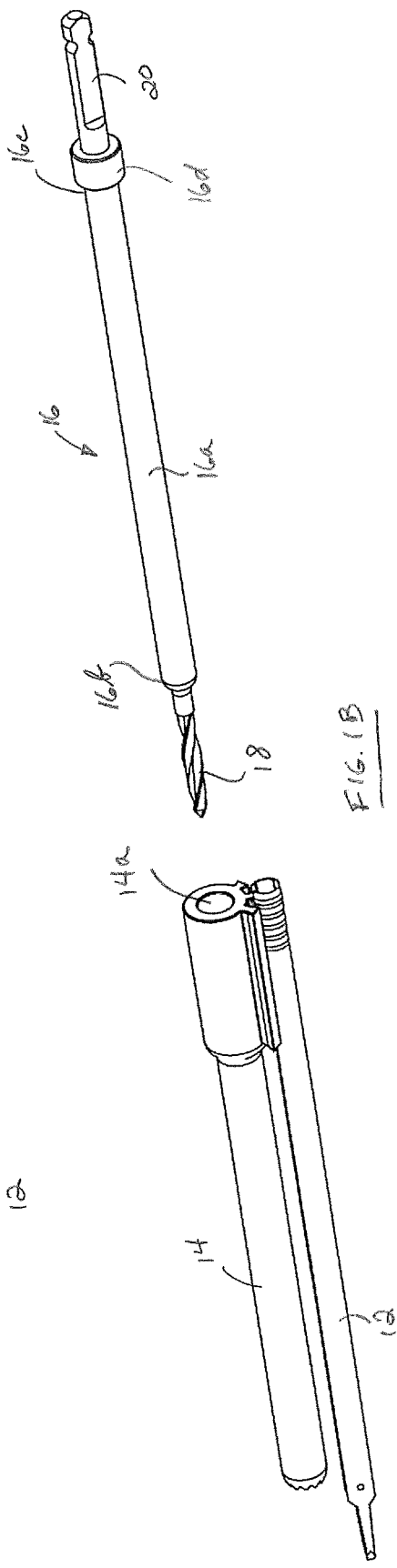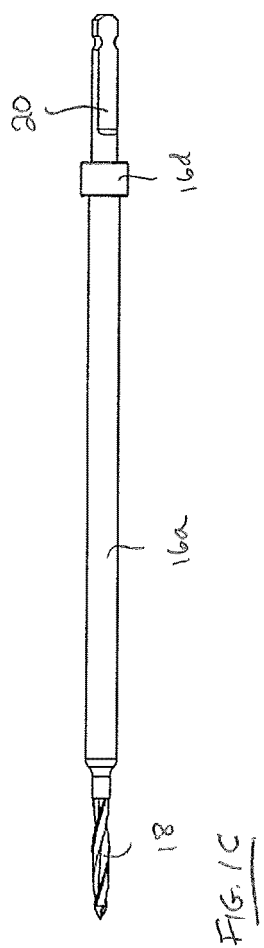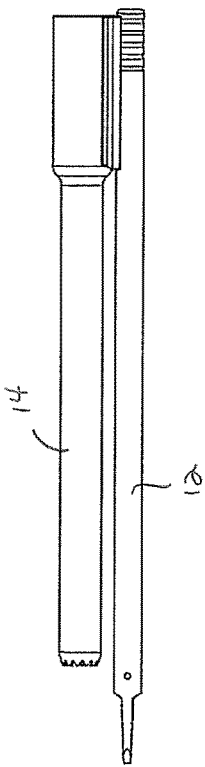

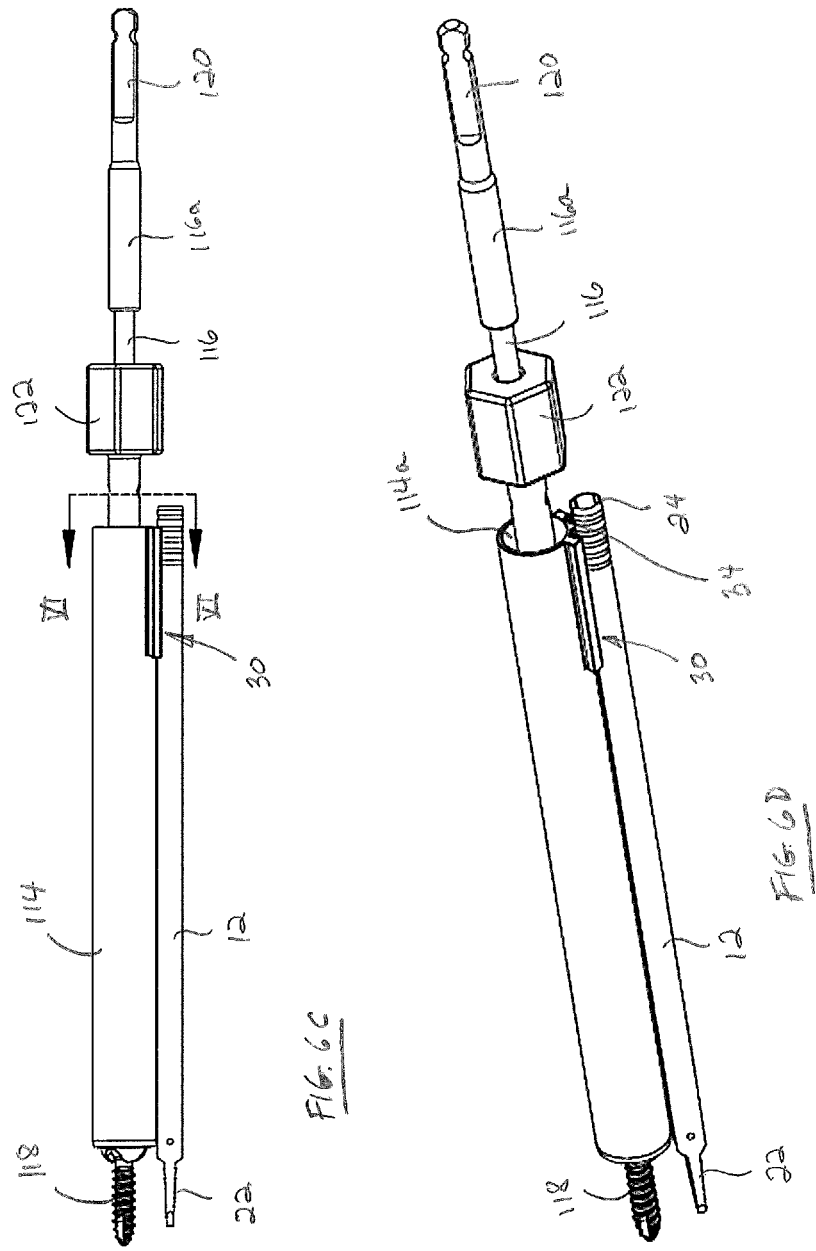

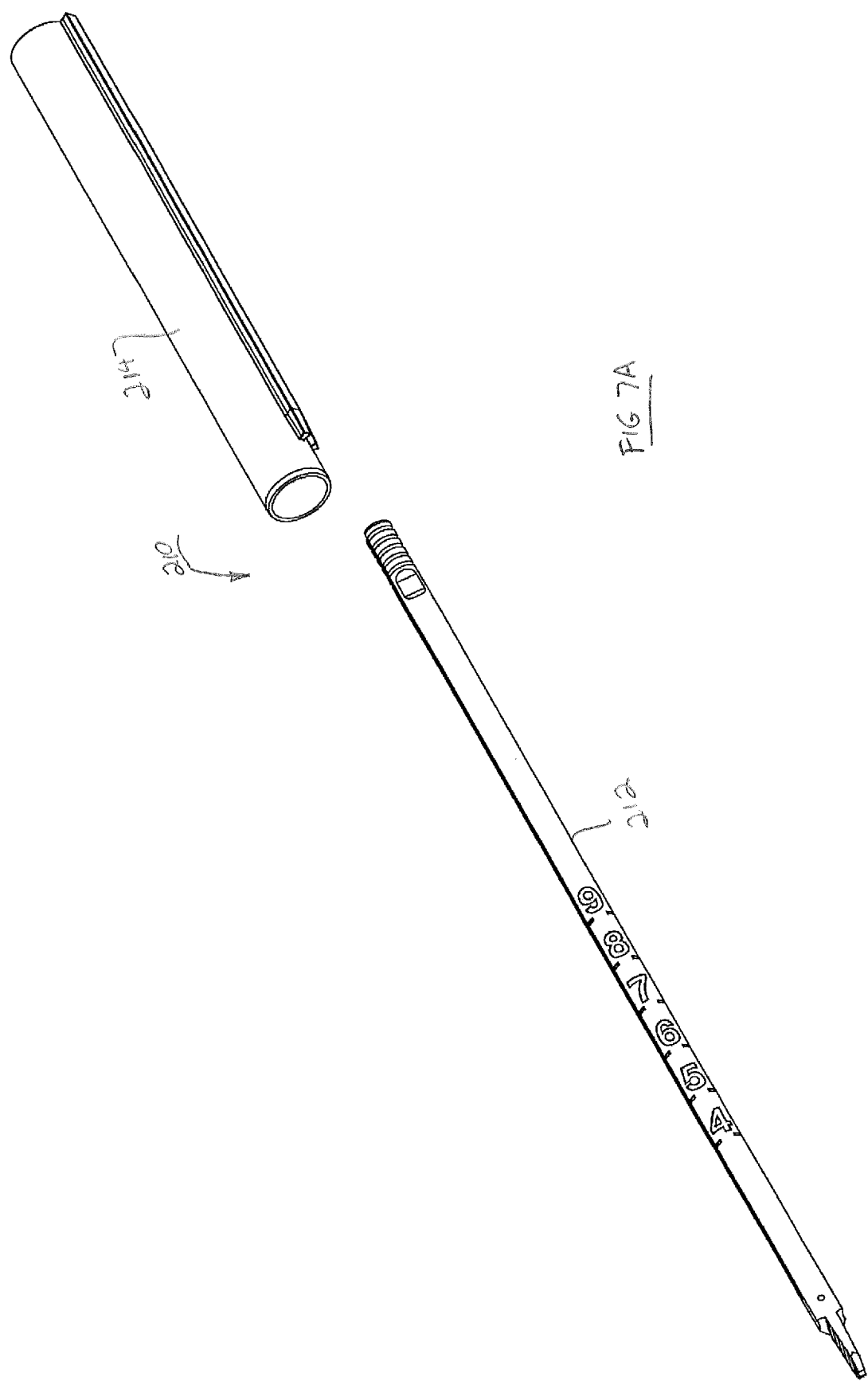

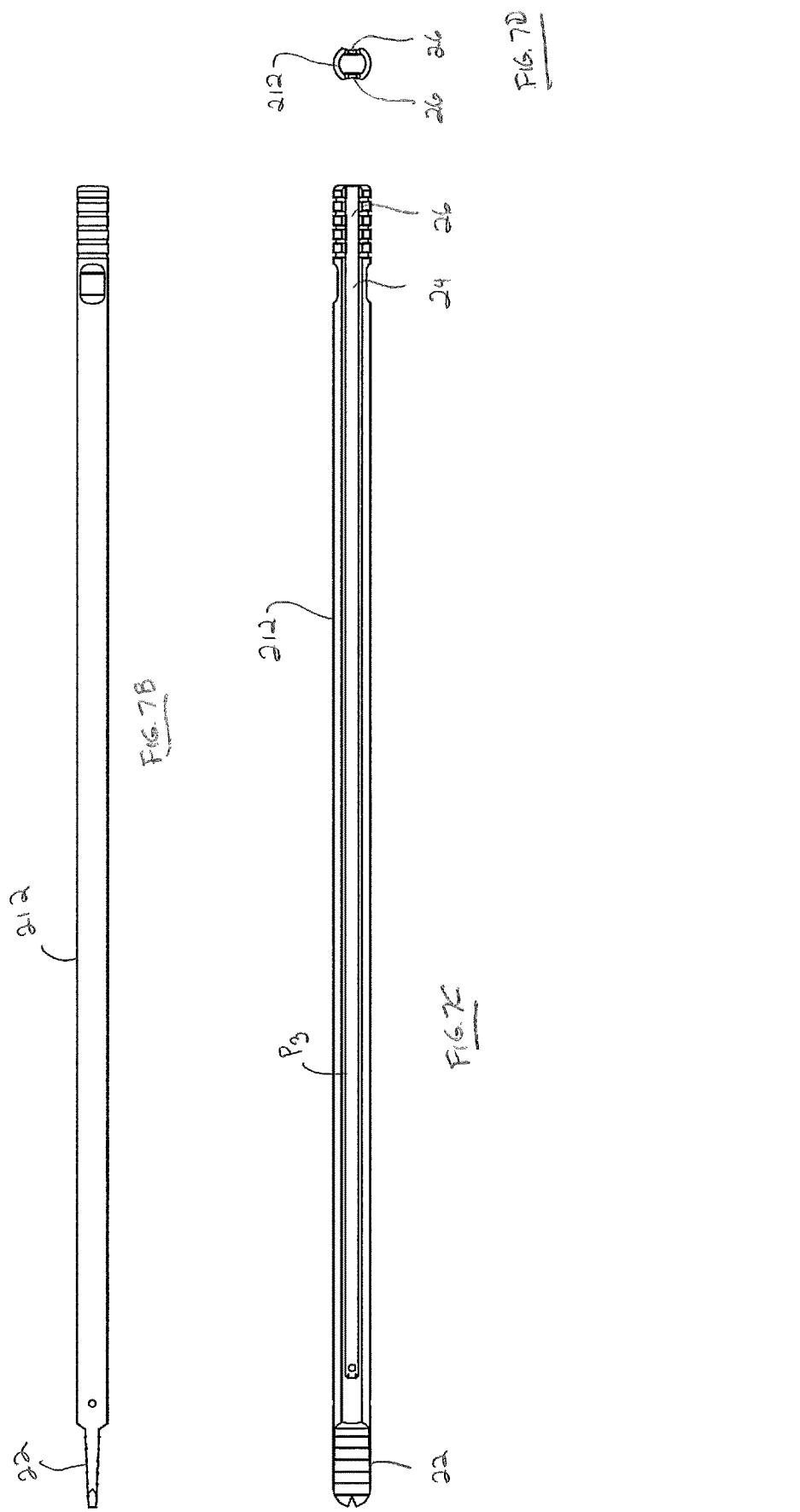

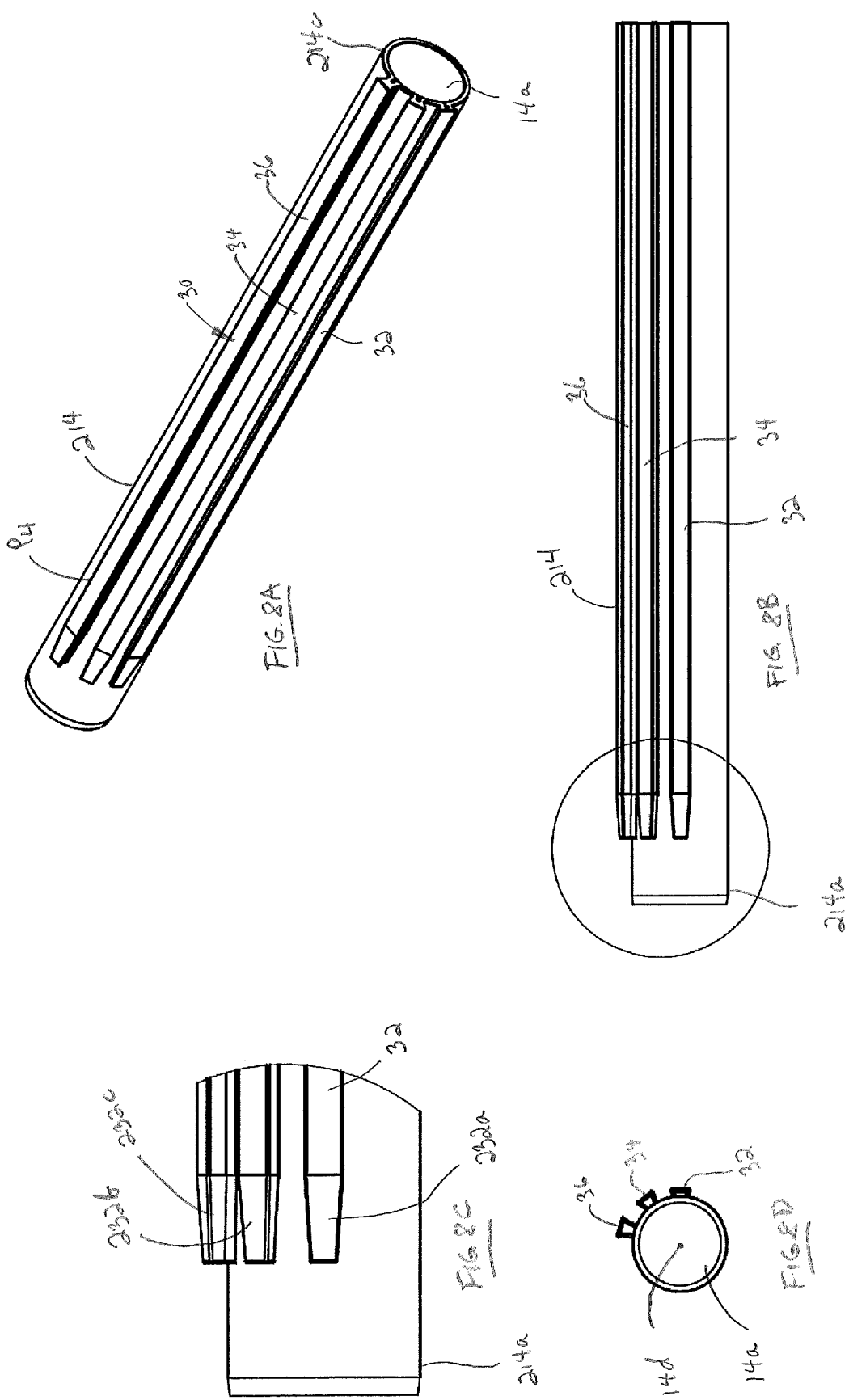

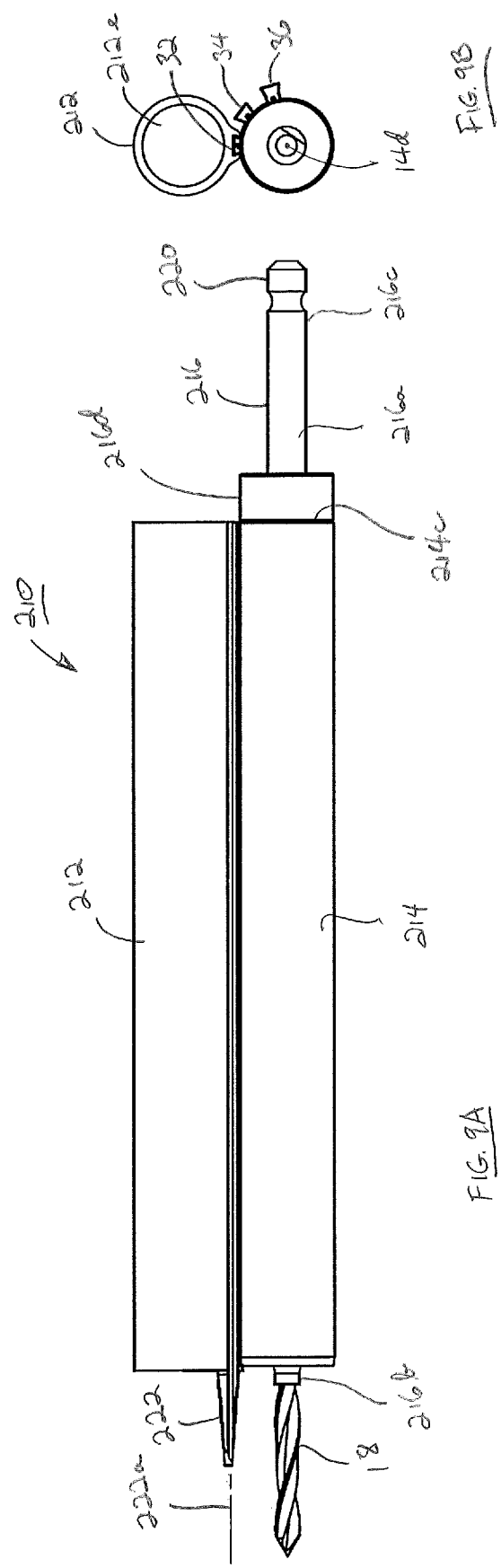

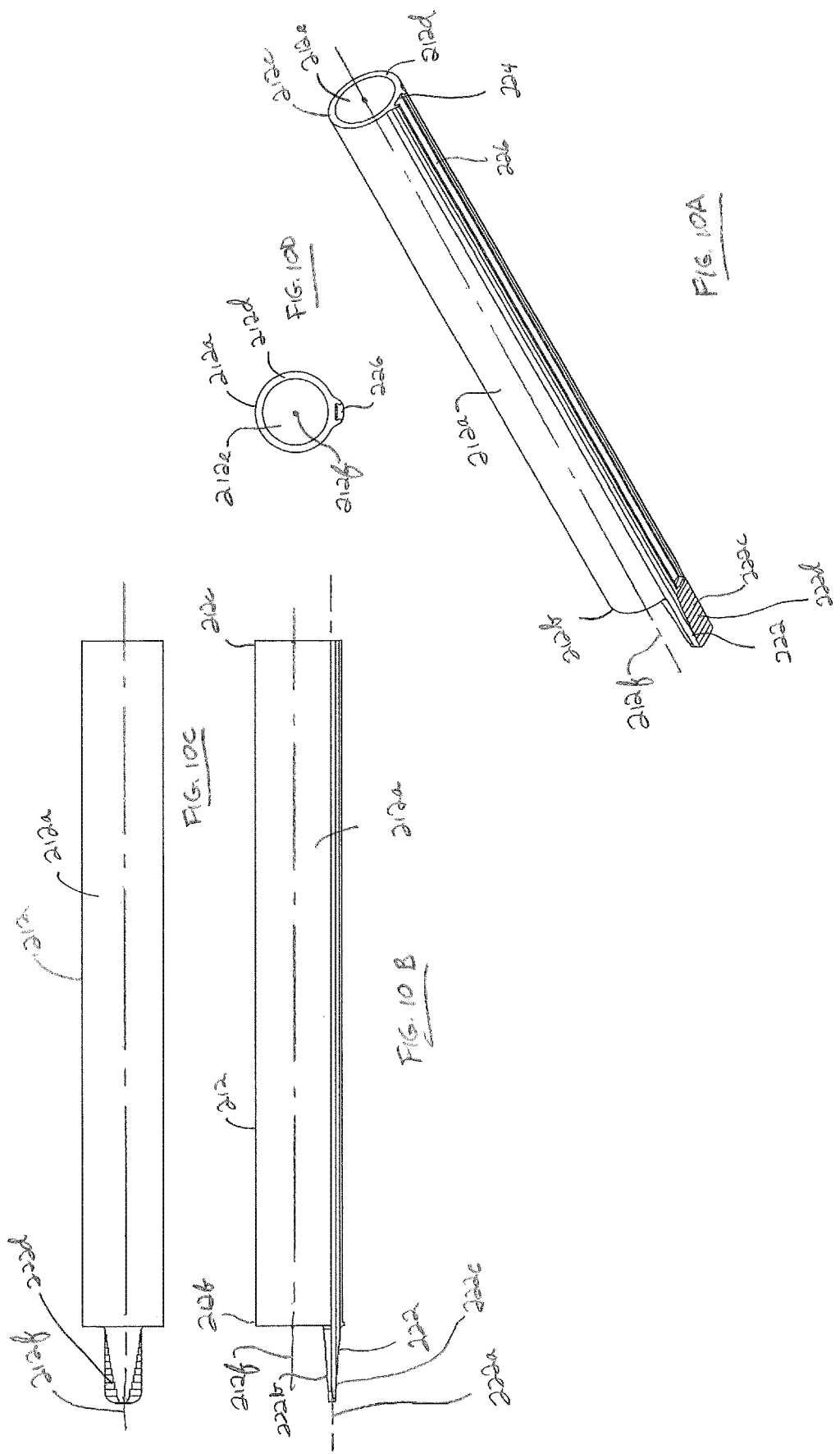

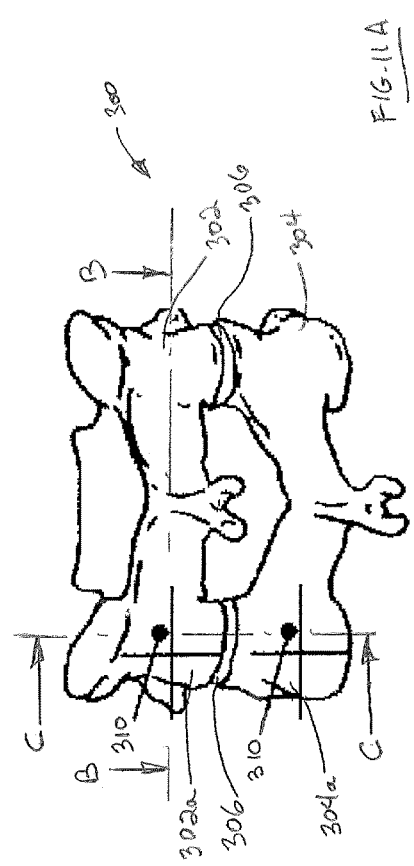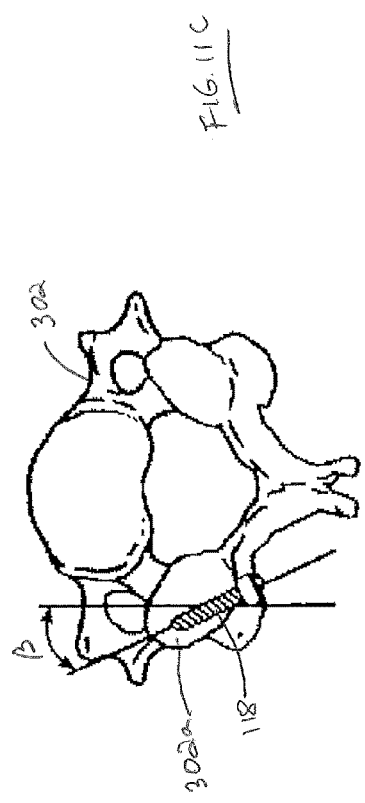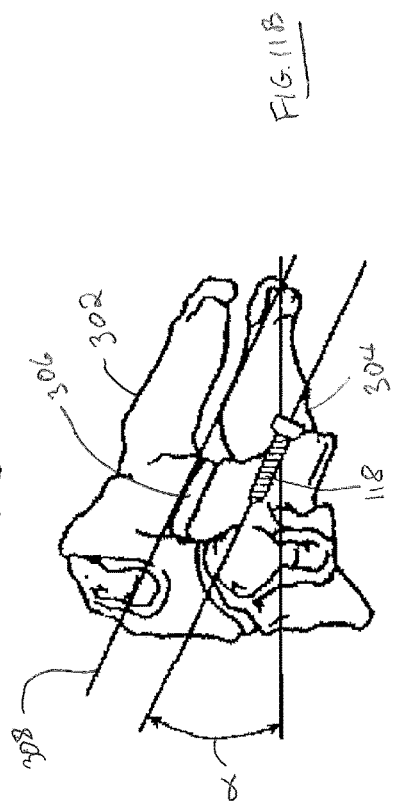

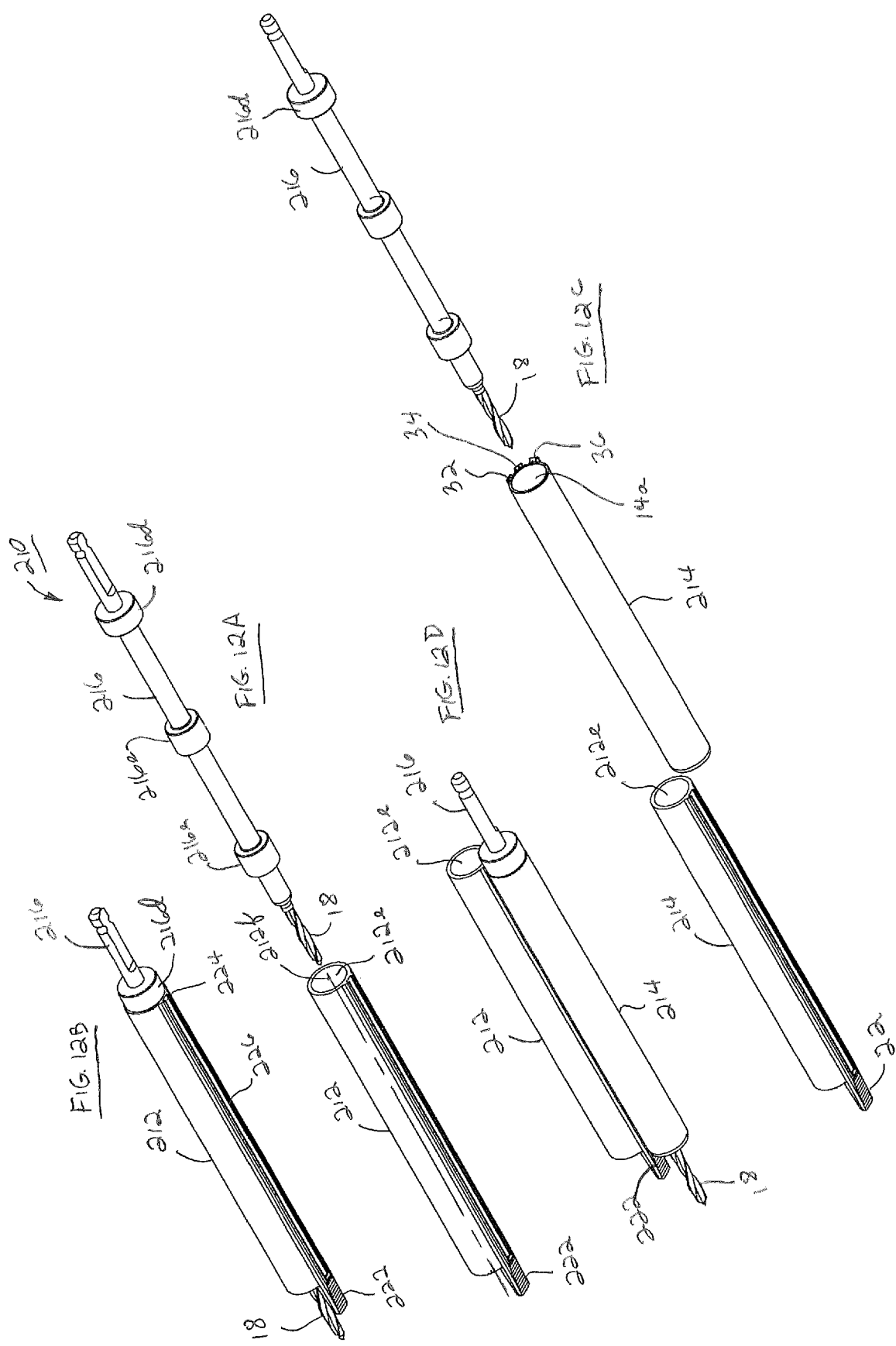

POSTERIOR CERVICAL FIXATION SYSTEM

CROSS-REFERENCE TO RELATED APPLICATION

This application claims the benefit of U.S. Provisional Patent Application No. 62/804,941, filed Feb. 13, 2019, the entire contents of which are incorporated by reference herein.

FIELD OF THE INVENTION

The subject invention relates to a system and method for accessing a surgical site, and more particularly to instrumentation that uses the facet joints to establish and guide the trajectory of a lateral mass screw in posterior cervical fusion.

BACKGROUND OF THE INVENTION

In U.S. Patent Publication No. 2019/0342648 entitled "Lateral Mass Fixation Implant", published Dec. 3, 2015, McCormack et al. describe a system and method for providing lateral mass fixation in the cervical spine using a posterior access. The inventors recognize that while anterior cervical spinal fusion is considered less traumatic, they believe that posterior cervical fusion with lateral mass screw or pedicle screw fixation provides a more rigid construct than anterior plates, interbody fusion or interspinous wiring. Nevertheless, the ability to ensure proper placement of fixation devices, especially in less invasive procedures has been found to be more difficult using the posterior access approach. For example, the starting of a pilot hole into the lateral mass and the subsequent tapping, drilling and introduction of a screw into the hole is tedious if the hole position is not maintained throughout the procedure. Accordingly, it is desirable to have a system and instrumentation that allows for the positioning and maintenance of a pilot hole position for subsequent steps that include the insertion of a lateral mass screw.

SUMMARY OF THE INVENTION

It is an object of the invention to provide an improved system and method for posterior cervical fusion.

In accordance with one aspect, the instrumentation of the subject system provides a facet lock technique that helps in guiding and maintaining the trajectory of a lateral mass screw, particularly in posterior cervicothoracic stabilization surgery. This technique has particular utilization between the C3 and C7 vertebra of the cervical spine. The instrumentation uses the trajectory of the facet joints anatomical boundaries to aid in drilling and placing screws and may be used in both open and mini-open surgical techniques.

Other objects and benefits of the invention will become apparent upon consideration of the following written description taken together with the accompanying figures.

DESCRIPTION OF THE FIGURES

FIG. 1A is a perspective view of a first embodiment of a posterior cervical fixation system of the subject invention.

FIGS. 1B and 1C are exploded perspective and side elevational views respectively of the system of FIG. 1A

FIGS. 6C and 6D are respective side and perspective views of the posterior cervical fixation system of FIGS. 6A and 6B with the lateral mass screw and screwdriver instrument assembled.

FIG. 7A is an exploded perspective view showing alternative arrangements of the facet lock and drill guide of the subject posterior cervical fixation system.

FIGS. 7B, 7C and 7D are respectively, a side elevational view, a top plan view and a proximal end view of the alternative facet lock of FIG. 7A FIG. 8A is a top perspective view of the alternative drill guide of the posterior cervical fixation system of FIG. 7A.

FIG. 8B is a side elevation view of the alternative drill guide of FIG. 8A.

FIG. 8C is an enlarged view of the encircled portion of the distal end of alternative drill guide of FIG. 8B.

FIG. 8D is an end view of the proximal end of the alternative drill guide of FIG. 8A.

FIG. 9A is a side elevational view of a posterior cervical fixation system in accordance with a second embodiment of the subject invention showing a tubular facet lock attached to the alternative tubular drill guide of FIG. 8A with an instrument supporting a drill received in the alternative tubular drill guide.

FIG. 9B is an end view of the proximal end of the system of FIG. 9A.

FIG. 10A is a bottom perspective view of the alternative facet lock of the second embodiment of the posterior cervical fixation system of FIG. 9A.

FIG. 10B is a side elevational view of the alternative facet lock of FIG. 10A.

FIG. 10C is top plan view of the alternative facet lock of FIG. 10A.

FIG. 10D is an end view of the proximal end of the alternative facet lock of FIG. 10A.

FIG. 11A is a schematic view of a posterior section of a cervical spine.

FIG. 11B is a sectional view taken along a transverse plane of the cervical spine as seen along viewing lines B-B of FIG. 12A.

FIG. 11C is a sectional view taken along a sectional plane of the cervical spine as seen along viewing lines C-C of FIG. 12A.

FIG. 12A is an exploded perspective view of the tubular facet lock of FIG. 9A positioned to receive an instrument supporting a drill.

FIG. 12B is a perspective view of FIG. 12A showing the instrument supporting the drill received in the tubular facet lock.

FIG. 12C is an exploded perspective view of the tubular facet lock of FIG. 9A and the alternative tubular drill guide of FIG. 8A positioned to receive the instrument supporting the drill.

FIG. 12D is a perspective view of FIG. 12C showing the tubular facet lock attached to the alternative tubular drill guide and the instrument supporting the drill received in the alternative tubular drill guide.

DESCRIPTION OF THE EMBODIMENTS

Figure 2A:
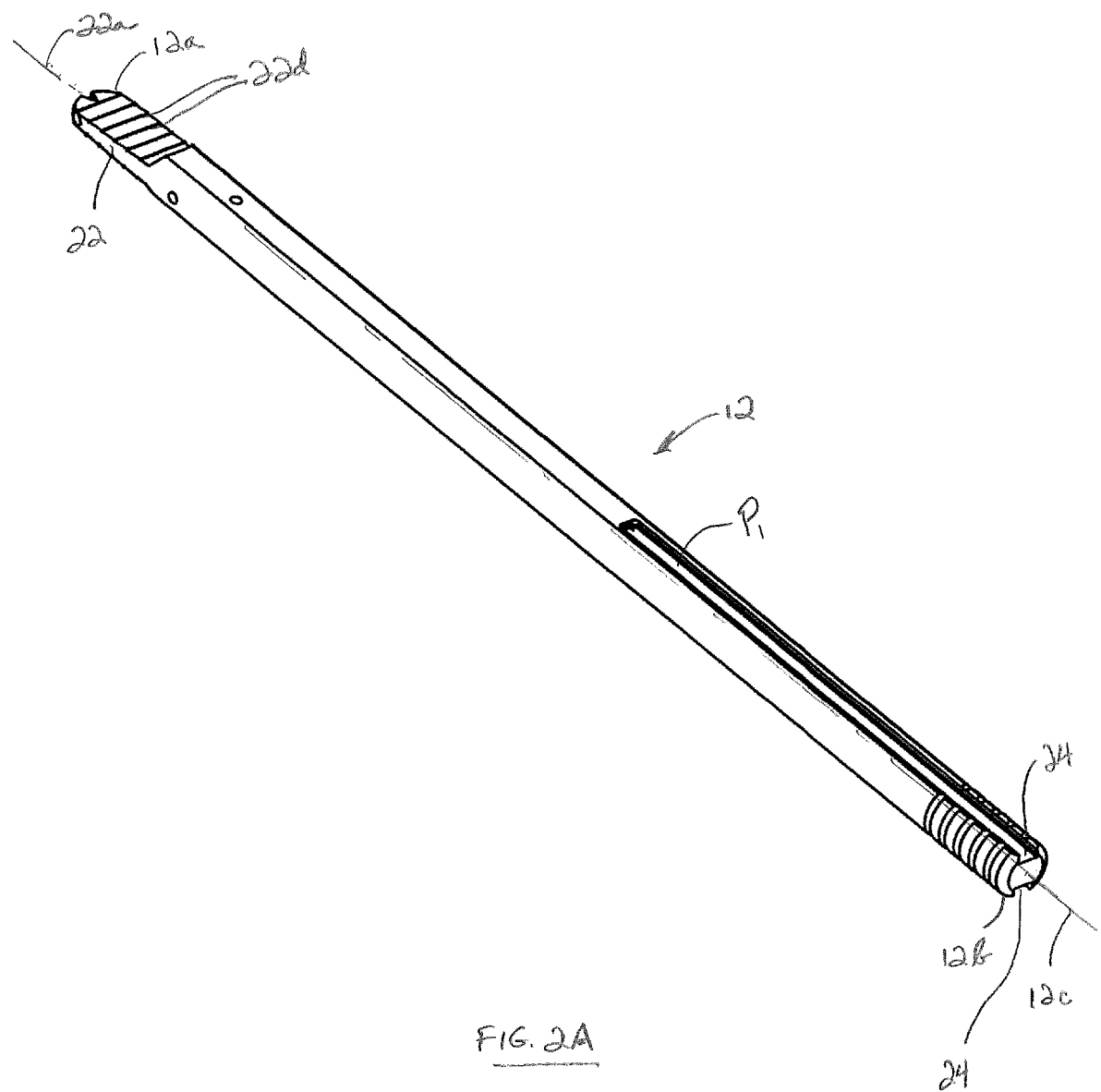
FIG. 2A is a top perspective view of a facet lock of the system of FIG. 1A.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Turning now to FIGS. 1A, 1B and 1C a posterior cervical system 10 is shown. In accordance with a first embodiment, system 10 comprises a facet lock 12 and a tubular guide 14 that are configured for cooperative releasable attachment to each other. Tubular guide 14 has a lumen 14a extending therethrough. In this particular arrangement shown, lumen 14a is sized and configured to receive an instrument 16 therein. Instrument 16 may have an elongate shaft 16a, a distal end 16b and a proximal end 16c. A tool bit 18, such as a drill or a tap is supported axially at the distal end 16b and a tool engagement surface 20 may be formed at the proximal end 16c. A stop 16d may be supported on shaft 16a to engage the proximal end of tubular guide 14 so as to limit the extent to which tool bit 18 may project distally beyond tubular guide 14. Engagement surface 20 may be connected to a suitable conventional external tool for rotating instrument 16 including tool bit 18 within lumen 14a to form a pilot hole in the lateral mass of a cervical vertebral body, as will be described. As will be further described hereinbelow, an additional tubular guide releasably attachable to facet lock 12 and sized and configured for receipt of a lateral mass screw may also be provided for releasable attachment to facet lock 12 after the formation of the pilot hole as part of the first embodiment of posterior cervical system 10.

Figure 2B:
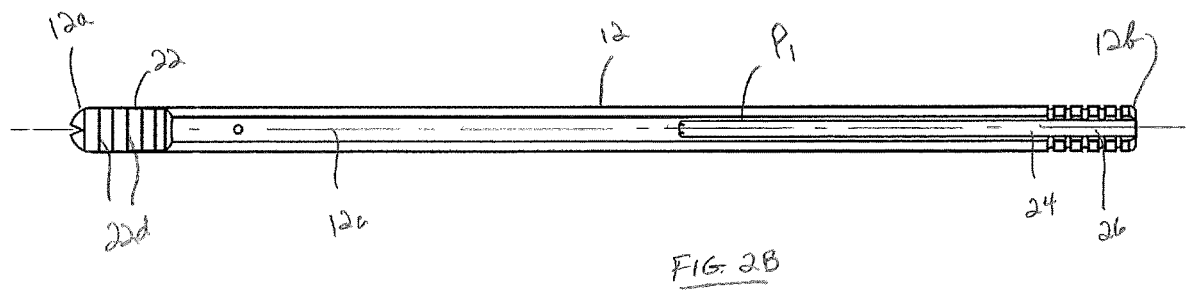
FIG. 2B is a top plan view of the facet lock of FIG. 2A
Figure 2C:
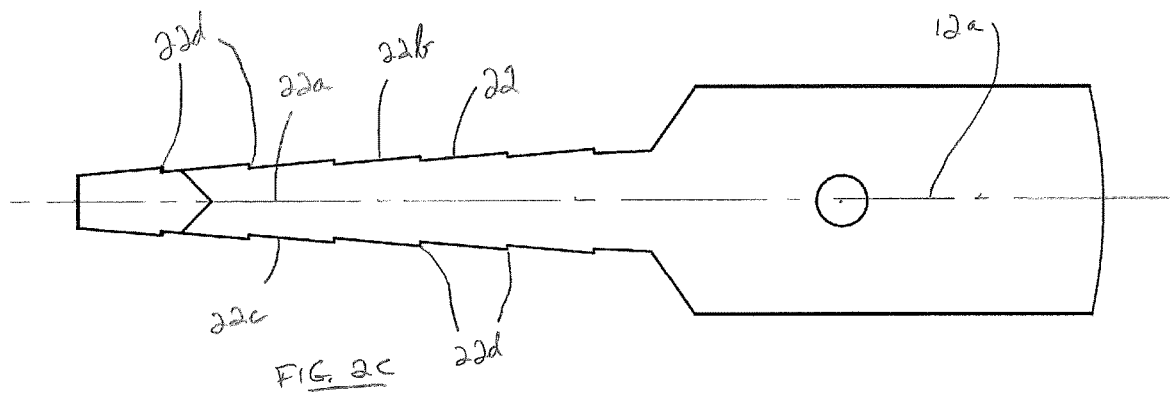
FIG. 2C is an enlarged view of the distal end of the facet lock of FIG. 2A showing details of a tapered wedge that is sized and configured for posterior insertion into a facet joint of a cervical spine.

Referring now to FIGS. 2A, 2B, 2C and 2D further details of facet lock 12 are described. Facet lock 12 is an elongate member having a distal end 12a, a proximal end 12b and a center longitudinal axis 12c extending therethrough. In this particular arrangement, facet lock 12 is non-cannulated with a solid cross-section. Facet lock 12 comprises a tapered wedge 22 projecting axially from the distal end 12a, tapered wedge 22 defining a wedge axis 22a, as shown in FIG. 2C. In this particular arrangement, wedge axis 22a is coincident with facet lock center longitudinal axis 12a, it being understood that wedge axis 22a and center longitudinal axis may be offset relative to each other. Tapered wedge 22 is sized and configured to be inserted into a facet joint of a cervical spine, as will be described, and includes an upper surface 22b and a lower surface 22c that are each inclined downwardly distally toward wedge axis 22a. It should be appreciated that only one of inclined surfaces 22b or 22c may be inclined while the other surface remains substantially parallel to center longitudinal axis 22a. Each of upper surface 22b and lower surface 22c is configured to have a series of serrations 22d formed thereon to assist in retaining tapered wedge 22 within the facet joint as well as to roughen opposing tissue surfaces of the opposing facets in a manner to promote fusion between the opposing facet tissue surfaces.

Figure 2D:
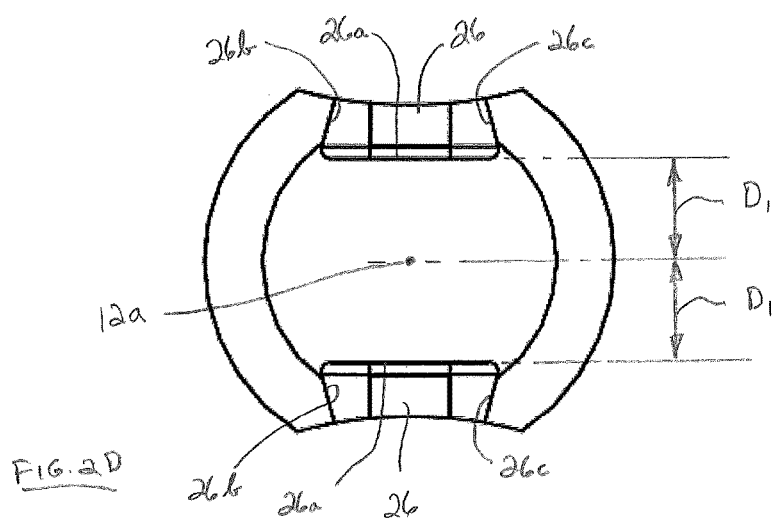
FIG. 2D is an enlarged end view of the proximal end of the facet lock of FIG. 2A

Facet lock 12 includes at the proximal end 12b an attachment feature 24 for releasable selective connection to tubular guide 14, as will be described. In a particular arrangement, there are two substantially opposite attachment features 24, one facing upwardly relative to tapered wedge 22, and the other facing downwardly. Each attachment feature 24 is in one configuration formed as a conventional dovetail recess 26 having a base 26a and a pair of inwardly inclined opposing surfaces 26b and 26c, as shown in FIG. 2D. As such, there are upper and lower substantially opposite dovetail recesses 26 shown. Each base 26a defines a substantially flat support surface, the purpose and function of which will be described, and is spaced from facet lock center longitudinal axis 12a by a fixed distance, Di. Each attachment feature 24 extends along facet lock 12 from proximal end 12b toward distal end 12a for a portion, $P_1$ of the length of facet lock 12, as shown in FIGS. 2A and 2B.

Figure 3B:
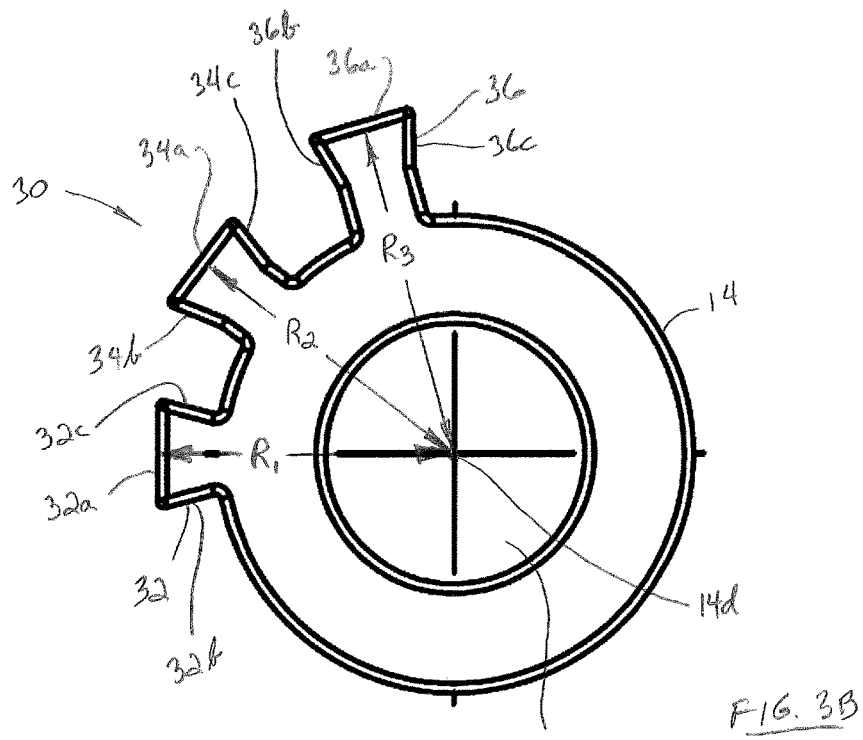
FIG. 3B is an enlarged end view of the proximal end of the drill guide of FIG. 3A.
Figure 3A:
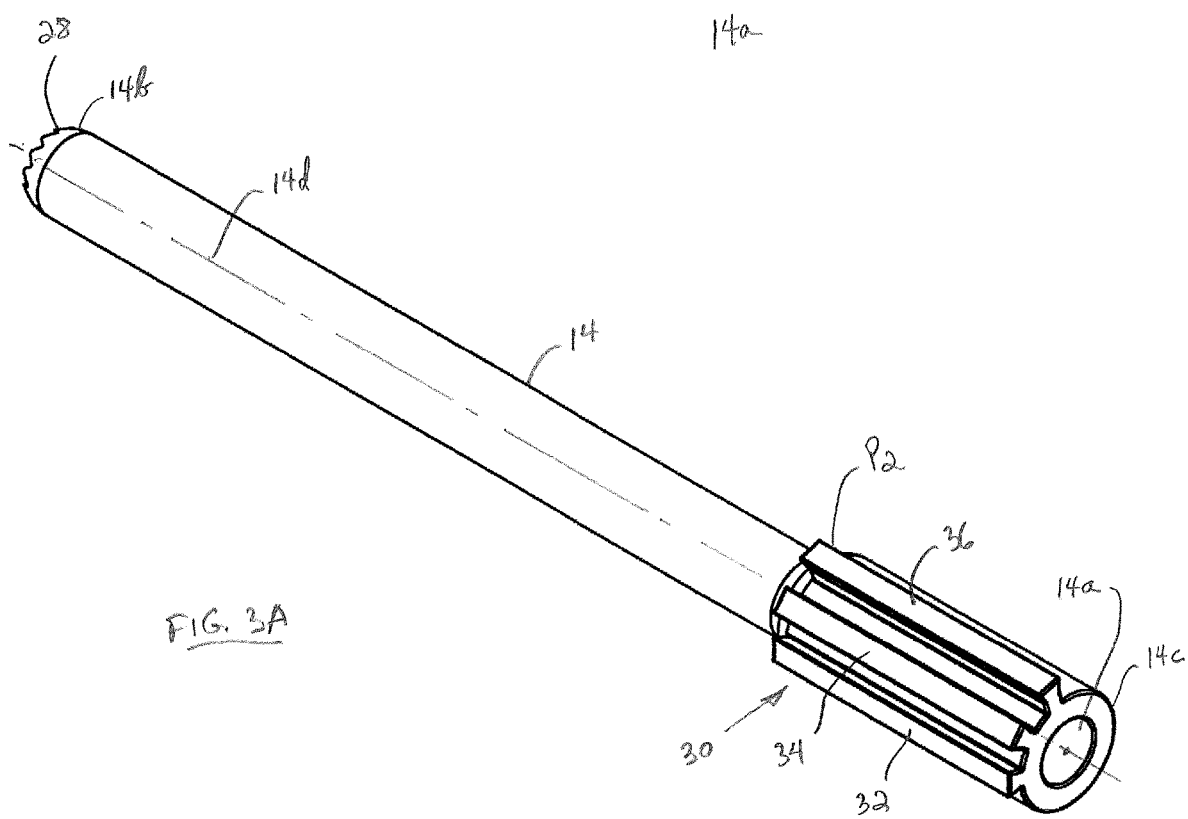
FIG. 3A is a perspective view of a tubular guide of the system of FIG. 1A that is sized and configured as a drill guide.

Turning now to FIGS. 3A and 3B, further details of tubular guide 14 are described. Tubular guide 14 is an elongate tubular member having a distal end 14b, a proximal end 14c with lumen 14a extending therethrough along a central axis 14d. In the particular arrangement shown, tubular member 14 is sized and configured, as noted hereinabove, to receive an instrument 16 that supports a tool bit 18, such as a tap or drill. Distal end 14b of tubular guide 14 may be formed to have a plurality of teeth 28 extending circumferential therearound and projecting axially therefrom. Teeth 28 may facilitate the securement of tubular guide 14 against facet tissue surfaces during use, as will be described. Tubular guide 14 includes at proximal end 14c a plurality of mating elements 30 extending radially outwardly from tubular guide 14 in a direction transverse to central axis 14d. In the particular arrangement shown in FIG. 3B, there are three mating elements 30 each of which is formed as a dovetail projection 32, 34 and 36 that is configured to be matingly individually and selectively received in a dovetail recess 26 of facet lock 12, as will be described. Each dovetail projection 32, 34 and 36 terminates respectively in a substantially flat engagement surface 32a, 34a and 36a and has a pair of outwardly inclined opposing surfaces 32b, 32c, 34b, 34c and 36b, 36c, as shown in FIG. 3B. Engagement surfaces 32a, 32b and 32c are each spaced at a different radial distances, $R_1$, $R_2$ and $R_3$, respectively, from said central axis 14a, as depicted in FIG. 3B. In this arrangement, distance $R_3$ is greater than distance $R_2$, and distance $R_2$ is greater than distance $R_1$. Mating elements 30 extend along tubular guide 14 from proximal end 14c toward distal end 14b for a portion, $P_2$ of the length of tubular guide 14, as shown in FIG. 3A. It should be appreciated that while there are three mating elements 30 shown, more or less mating elements 30 may be provided within the contemplated invention.

Figure 4A:
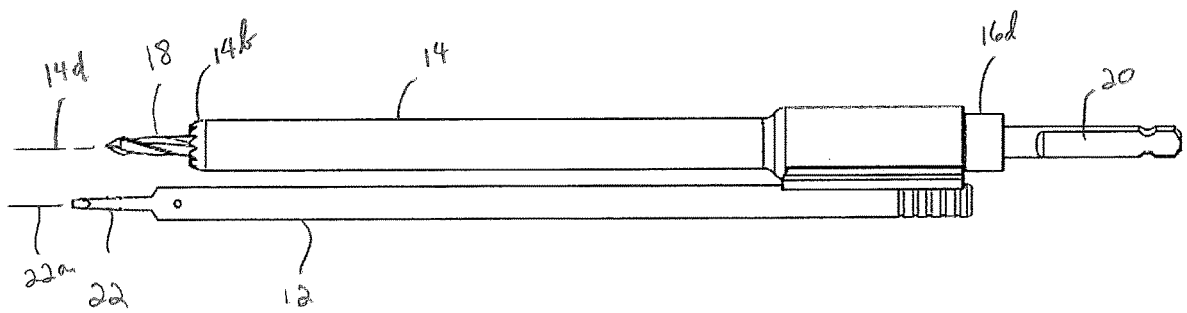
FIG. 4A is a side elevational view of the system of FIG. 1A
Figure 4B:
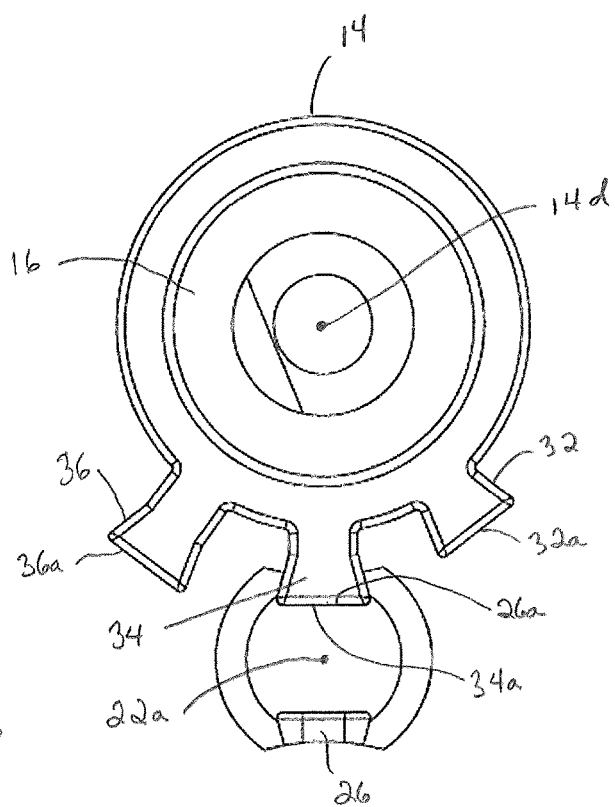
FIG. 4B is an enlarged end view of the proximal end of the system of FIG. 1A showing details of the attachment of the facet lock of FIG. 2A and the drill guide of FIG. 3A.

With reference now to FIGS. 4A and 4B, the attachment of facet lock 12 and tubular guide 14 is illustrated. One of dovetail projections 32, 34 or 36 may be selected during use for attachment to one of upper or lower dovetail recesses 26 of facet lock 12. In the particular arrangement shown in FIG. 4B, dovetail projection 34, for example, has been selected for attachment with upper dovetail recess 26. To effect attachment, dovetail projection 34 is slid axially within upper recess 26 along the length portion $P_1$ until it bottoms out as illustrated in FIG. 4A. In attachment, flat engagement surface 34a of dovetail projection 34 engages flat base 26a of upper dovetail recess 26, thereby supporting dovetail projection 34 therewithin and establishing a particular spacing between wedge axis 22a of facet lock 12 and central axis 14d of tubular guide 14. Having established such a spacing, instrument 16 may be introduced into tubular guide 14 such that tool bit 18 projects along tubular guide axis 14d through distal end 14b of tubular guide 14. In this manner the spacing between tool bit 18 and wedge axis 22a is selected as desired in use. It should be understood that any of the dovetail projections 32, 34 or 36 may be chosen for attachment to either upper or lower dovetail recesses 26 of facet lock 12. The different spacings achievable are illustrated with reference to FIGS. 5A, 5B and 5C.

Figure 5A:
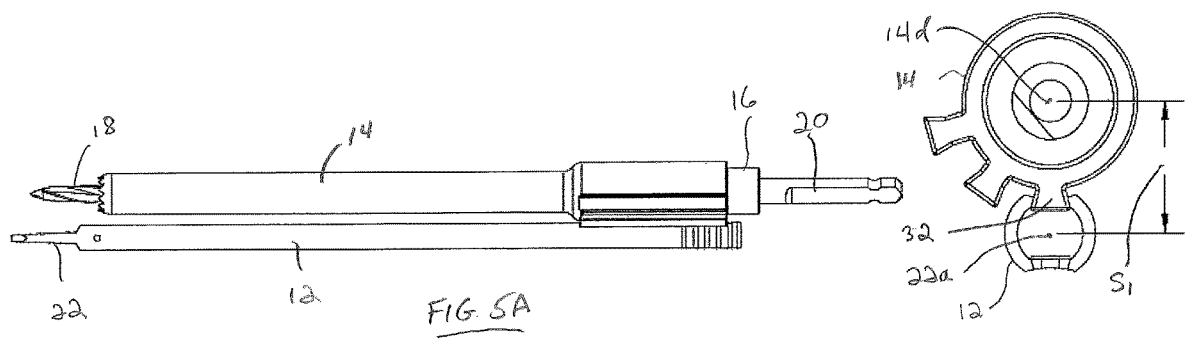
FIGS. 5A, 5B and 5C each illustrate side and end views of the facet lock and drill guide in one of three different attachment configurations.
Figure 5B:
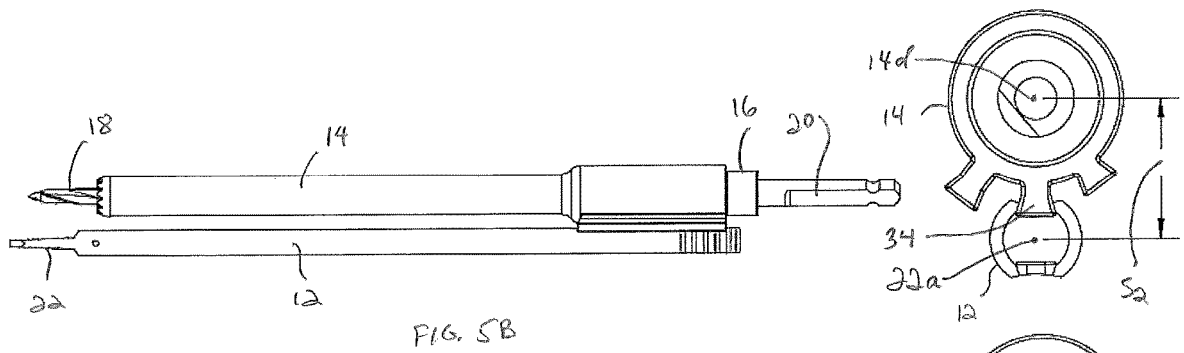
Figure 5C:
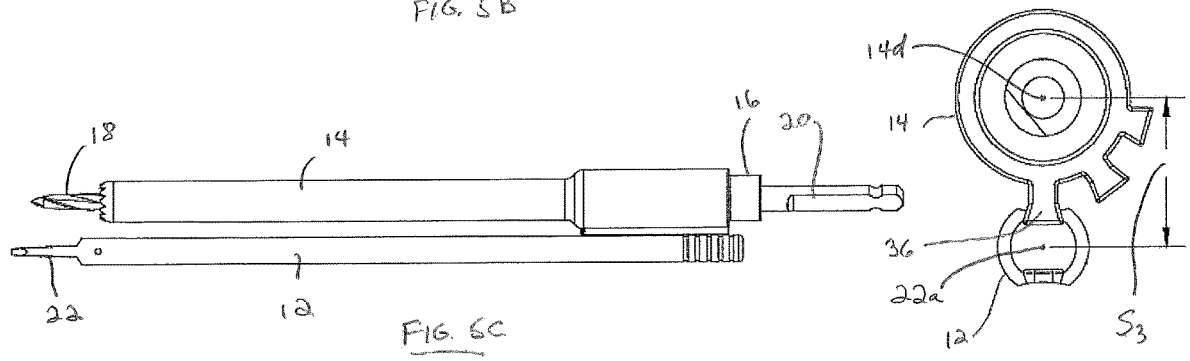

As depicted in FIG. 5A, projection 32 is received within upper dovetail recess 26 as described with reference to FIG. 4B. This attachment will result in a spacing $S_1$ between tubular guide central axis 14d and wedge axis 22a. In FIG. 5B, projection 34 is received within upper dovetail recess 26 resulting in a spacing $S_2$ between tubular guide central axis 14d and wedge axis 22a. In FIG. 5C, projection 36 is received within upper dovetail recess 26 resulting in a spacing $S_3$ between tubular guide central axis 14d and wedge axis 22a. Due to the different radial dimensions $R_1$, $R_2$ and $R_3$, of dovetail projections 32, 34 and 36 as described hereinabove, spacings $S_1$, $S_2$ and $S_3$ will likewise be different. In this arrangement described, spacing $S_1$ will be less than $S_2$, while spacing $S_2$ will be less than spacing $S_3$. By way of example only, facet lock 12 and tubular guide 14 may be dimensioned such that in attachment, spacing $S_1$ will be 0.302 inches, spacing $S_2$ will be 0.322 inches and spacing $S_3$ will be 0.342 inches. Accordingly, it should be appreciated that mating elements 30 may be individually selected for releasable attachment to one of the two attachment features 24 of facet lock 12 to selectively space wedge axis 22d and central axis 14d of tubular guide 14 at different distances.

Turning now to FIGS. 6A, 6B, 6C, 6D and 6E, an additional tubular guide 114 of the first embodiment is shown in attachment with facet lock 12 to provide a facet screw placement guide. Tubular guide 114 may be attached to facet lock 12 after a pilot hole has been drilled in a lateral mass of a cervical body in a manner to introduce a lateral mass screw into the pilot hole along the same axis 14d established by tool bit 18. Tubular guide 114 is substantially identical in structure to tubular guide 14, including central axis 14d and the plurality of mating elements 30, except that lumen 114a is sized and configured to receive a lateral mass screw 118 and a screwdriver instrument 116, as illustrated. As such, common features of tubular guide 14 and tubular guide 114 will have like reference numerals.

In a particular arrangement, lateral mass screw 118 comprises a yoke 118b attached thereto for relative polyaxial movement. Yoke 118b may have extended breakaway tabs 118c that facilitate reception of a fixation rod (not shown) in a manner to be secured in yoke 118 to stabilize the facet joint for fusion. The diameter of lumen 114a is formed to relatively closely receive yoke 118ba and extended tabs 118c. Screwdriver instrument 116 may have an elongate shaft 116a, a distal end 116b and a proximal end 116c. A screw engagement surface 116d may be formed at distal end 116b for attachment to lateral mass screw 118. A tool engagement surface 120 may be formed at the proximal end 116c. Tool engagement surface 120 may be connected to a suitable conventional external tool for rotating instrument 116 and thereby lateral mass screw 118 for threaded attachment within the pilot hole formed in the lateral mass of a cervical vertebral body, as will be described. A knob 122 may be supported on shaft 116a to assist in the manual attachment of screw engagement surface 116d into lateral mass screw yoke 118b and the subsequent introduction into the lumen 114a of screw placement tubular guide 114.

Figure 6A:
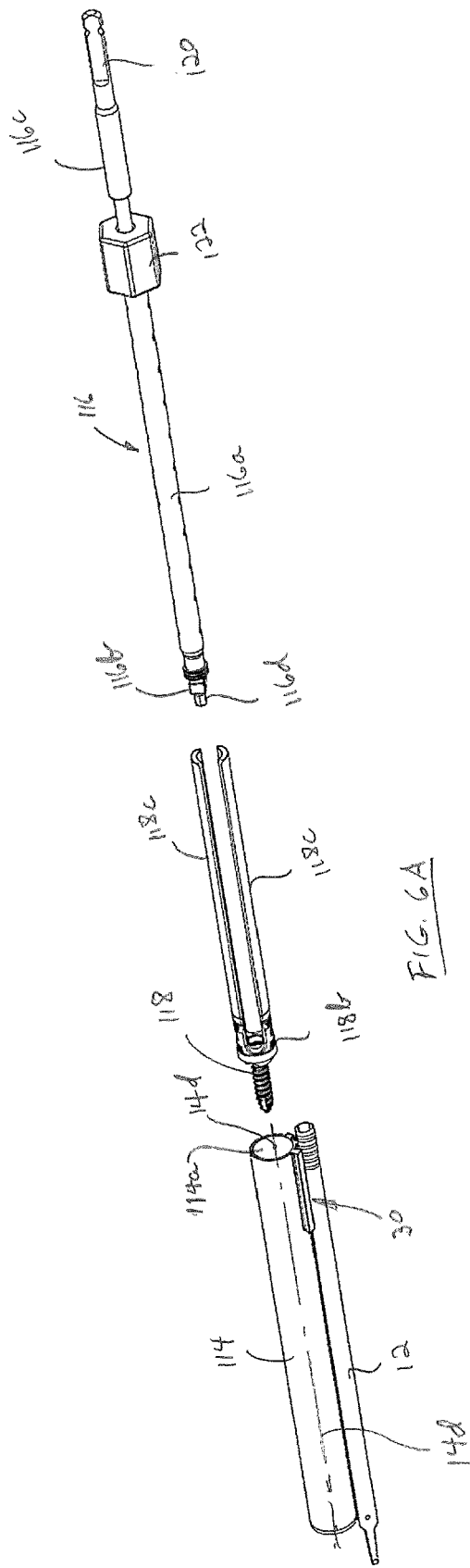
FIG. 6A is a perspective view of the posterior cervical fixation system with the facet lock of FIG. 2A in attachment with an additional tubular guide sized and configured as a facet screw placement guide and showing a lateral mass screw and screwdriver instrument in exploded disposition.
Figure 6B:
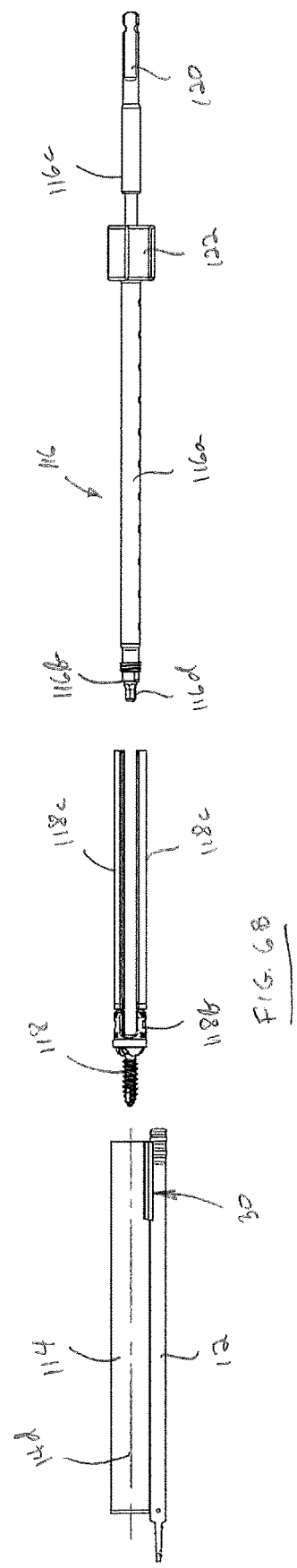
FIG. 6B is a side elevational view of the exploded view of FIG. 6A
Figure 6E:
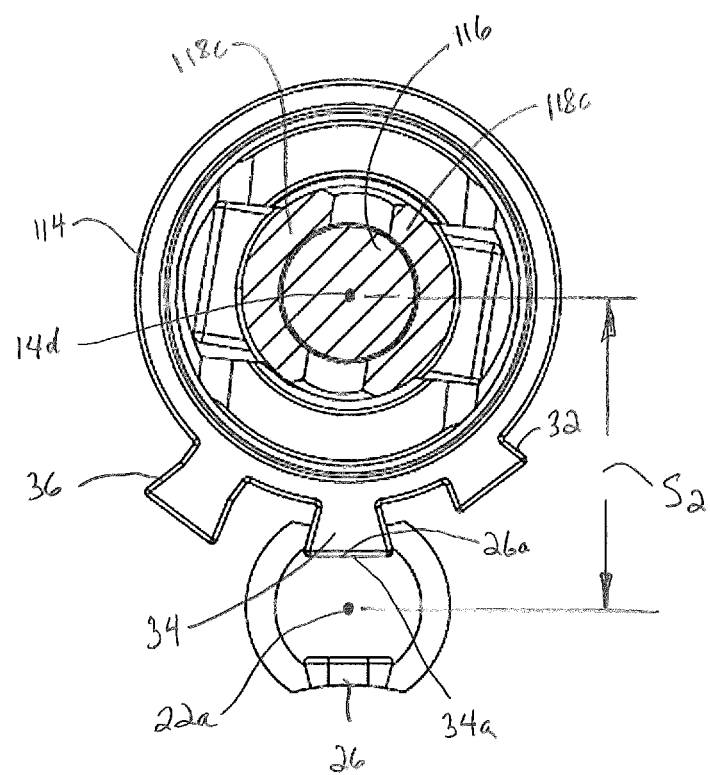
FIG. 6E is a cross-sectional view of the assembly of FIG. 6D as seen along viewing lines VI-VI of FIG. 6C

In FIGS. 6C and 6D screw placement tubular guide 114 is shown in attachment to facet lock 12 with lateral mass screw 118 supported by screwdriver instrument 116 having been introduced into lumen 114a of screw placement tubular guide 114. In this particular arrangement, dovetail projection 34 has been selected for insertion into facet lock upper dovetail recess 26. As such, and as shown in FIG. 6E, the spacing between central axis 14d of screw placement tubular guide 114 is $S_2$, the same spacing achieved with the attachment of tubular guide 14 to facet lock 12 using dovetail projection 34 of tubular guide 14, as shown in FIG. 5B. Accordingly, the axis along which lateral mass screw 118 will be introduced is the same axis along which a pilot hole was formed into the lateral mass of a cervical vertebral body by tool bit 18. It should be appreciated that while a tubular guide 14 may be used with tool bit 18 such as a drill to form a pilot hole in the cervical vertebral body lateral mass and a separate screw placement tubular guide 114 may be used to insert a lateral mass screw 118, a single tubular guide attachable to facet lock 12 may be used for both purposes.

Referring now to FIG. 7A, an alternative arrangement of the subject posterior cervical fixation system is shown. In this arrangement, posterior cervical fixation system 210 comprises facet lock 212 and a tubular guide 214 that is releasably attachable to facet lock to 212. As further detailed in FIGS. 7B, 7C and 7D, alternative facet lock 212 is substantially identical in structure to facet lock 12, except for the length of attachment features 24 As such, common features of facet lock 12 and facet lock 112 will have like reference numerals. In facet lock 112, attachment features 24 defined by upper and lower dovetail recesses 26 extend along a longer portion $P_3$ of the length of facet lock 212 than in facet lock 12. The length of portion $P_3$ runs nearly the entire length of facet lock 212, and at least over the majority of the length of facet lock 212. The additional length provides for a more rigid and stable attachment to alternative tubular guide 214, which as described below, also includes mating elements 30 having longer lengths.

As shown in FIGS. 8A, 8B, 8C and 8D, alternative tubular guide 214 is substantially identical in structure to tubular guide 14, except for the length of mating elements 30 and the formation of such mating elements 30 adjacent the distal end 214a of tubular guide 214. As such, common features of tubular guide 214 and tubular guide 14 will have like reference numerals. In tubular guide 214, mating elements 30 defined by dovetail projections 32, 34 and 36 extend along a longer portion $P_4$ of the length of tubular guide 214 than on tubular guide 14. The length of portion $P_4$ runs nearly the entire length of tubular 214, and at least over the majority of the length of 214. The additional length provides for a more rigid and stable attachment to either of the attachment features 24 of facet lock 212. Further, each of dovetail projections 32, 34 and 36 are tapered at their distal end 232a, 234a and 236a in the axial direction adjacent the distal end 214a of tubular guide 214a, as shown in FIG. 8C. The tapered ends 232a, 234a and 236a facilitate entry of a selected mating element 30 into a selected dovetail recess 26 of facet lock 212.

Turning now to FIGS. 9A and 9B, a posterior cervical system 210 is shown in accordance with a second embodiment of the invention. System 212 comprises a tubular facet lock 212 attached to the alternative tubular guide 214, described above, that are configured for cooperative releasable attachment to each other. Tubular guide 214 has a lumen 14a extending therethrough that as described is sized and configured to receive an instrument, such as instrument 216 therein. Instrument 216 may have an elongate shaft 216a, a distal end 216b and a proximal end 216c. A tool bit 18, such as a drill or a tap may be supported axially at the distal end 216b and a tool engagement surface 220 may be formed at the proximal end 216c. A stop 216d may be supported on shaft 216a to engage the proximal end 214c of tubular guide 214 so as to limit the extent to which tool bit 18 may project distally beyond tubular guide 214. Engagement surface 220 may be connected to a suitable conventional external tool for rotating instrument 216 including tool bit 18 within lumen 14a to form a pilot hole in the lateral mass of a cervical vertebral body, as described above. In this particular arrangement, tubular guide 214 may also be used to introduce a lateral mass screw into the formed pilot hole, such that tubular guide 214 serves the dual purpose of providing a drill guide as well as a screw placement guide.

Referring now to FIGS. 10A, 10B, 10C and 10D, details of the tubular facet lock 212 of the second embodiment are described. Tubular facet lock 212 comprises an elongate tube 212a having a distal end 212b and a proximal end 212c. Tube 212a includes a peripheral wall 212d defining a lumen 212e extending therethrough along a central axis 212f. A tapered wedge 222 projects axially from peripheral wall 212d at the distal end 212b of elongate tube 212a, tapered wedge 222 defining a wedge axis 222a, as shown in FIG. 10B. In this particular arrangement, wedge axis 222a is substantially parallel to and offset from central axis 212f. Similar to tapered wedge 22 of facet lock 12, tapered wedge 222 is sized and configured to be inserted into a facet joint of a cervical spine, as will be described, and includes an upper surface 222b and a lower surface 222c that are each inclined downwardly distally wedge axis 222a. Each of upper surface 222b and lower surface 222c is configured to have a series of serrations 222d formed thereon to assist in retaining tapered wedge 222 within the facet joint as well as to roughen opposing tissue surfaces of the opposing facets in a manner to promote fusion between the opposing facet tissue surfaces.

Elongate tube 212a of tubular facet lock 212 includes at the proximal end 212c an attachment feature 224 for releasable selective connection to tubular guide 214. Attachment feature 224 has a dovetail recess 226 that is formed in an identical manner as dovetail recess 26 described hereinabove with respect to facet lock 12. In this arrangement however, recess 226 extends substantially along the entire length of elongate tube 212a from proximal end 212c to tapered wedge 222. Dovetail recess 226 is substantially axially aligned with tapered wedge 222, as shown in FIG. 10A. In this embodiment, tubular facet lock 212 may be used as a drill guide to receive a tool bit such as a drill to form a pilot hole in the vertebral lateral mass, as well as a screw placement guide to introduce a lateral mass screw into the formed pilot hole.

Having described the structure and function of the subject posterior cervical system herein, methods of using both embodiments 10 and 210 are described. FIG. 11A schematically illustrates a view of a posterior section 300 of a cervical spine. Each of vertebral bodies 302 and 304 includes a superior lateral mass 302a and an inferior lateral mass 302b each terminating in an articular facet separated by a facet joint 306 on each lateral side of the spine. Where facet fixation has been indicated for treatment, access to the facet joint is desirable to stabilize the joint. Posterior access and stabilization with lateral mass screw or pedicle screw fixation, as noted above, may provide a more rigid construct than anterior plates. To stabilize the facet joints and promote fusion, posterior cervical system 10 may be used as follows.

Using fluoroscopy, a trajectory 308 along the path of the facet joint is established, as depicted in FIG. 11B. Initially an incision is made caudally of a facet joint 306 to be stabilized on one lateral side of the spine with such incision being formed along the axis of trajectory 308. Tissue is retracted to expose the spinal segment adjacent the facet joint, such as facet joint 306, to be stabilized. Facet lock 12 is introduced into the surgical site along trajectory 308 and tapered wedge 22 is pressed into facet joint 306. Typically, the superior facet will be surgically addressed initially. The optimal entry point 310 of a pilot hole and hence lateral mass screw 118 is about 1-2 mm medially and cranially from the center of the lateral mass, as shown in FIG. 11A. Tubular guide 14 is made ready for attachment to facet lock 12. Considering the anatomy of the patient, one of the dovetails 32, 34 or 36 of tubular guide 14 that will provide the closest proximity to the designated entry point 310 is chosen. The selected dovetail projection, e.g. dovetail projection 34, is then slid into the upper dovetail recess 26 of facet lock 12 through the incision until teeth 28 at the distal end 14b of tubular guide 14 engage and bite into superior lateral mass 302a.

An instrument 16 with drill 18 is then inserted through the lumen 14c of tubular guide 14 to form a pilot hole into the superior lateral mass 302a. Instrument 16 with drill 18 attached thereto is rotated by an external tool through the attachment with tool engagement surface 20. The drill 18 is then removed from tubular guide 14, and tubular guide 14 is removed from facet lock 12. Screw placement guide 114 is then made ready for use. The same dovetail projection selected for use with tubular guide 14, e.g., projection 34, is then selected for use with screw placement guide 114. Screw placement guide 114 is then attached to facet lock 12 by sliding the selected dovetail projection, e.g. projection 34, into the upper dovetail recess 26 of facet lock 12. A lateral mass screw 118 is suitably loaded onto a screwdriver instrument 116 and lateral mass screw 118 is then introduced through screw placement guide 114 and threaded into the formed pilot hole by an external tool. Screwdriver instrument 116 is then disconnected from lateral mass screw 118 leaving lateral mass screw 118 in place. Thus, lateral mass screw 118 is placed along a path that is substantially parallel to the trajectory 308 of the facet joint 306 with the angle of placement having an upward angle, α of between 20-40°, as shown in FIG. 11B. As so placed, lateral mass screw 118 would typically be positioned at an angle, β of between 20-30° diverging laterally and parallel to the superior facet in the direction of the anterolateral border of the superior facet. A similar procedure is then performed to place a lateral mass screw 118 into the inferior lateral mass 304a using lower dovetail recess 26 of facet lock 12. Once a lateral mass screw 118 has been inserted into each of the superior and inferior lateral masses a suitable fixation rod (not shown)

may be secured to both screws 118 in a manner to stabilize the treated spinal segment. Optionally, a similar procedure may be performed on the opposite lateral segment of the spine whereby two lateral mass screws 118 are respectively inserted into superior and inferior lateral masses which are then secured by a further fixation rod.

Accordingly, it should be appreciated that the subject instrumentation of posterior cervical system 10 allows the lateral mass screw entry point in both superior and inferior lateral masses to be positionally adjusted to best fit the anatomy of the patient. In addition, use of the trajectory of the facet joint's anatomical boundaries aids in the drilling of pilot holes and placement of lateral mass screws without the loss of the surgical site during the procedure.

Turning now also to FIGS. 12A, 12B, 12C and 12D, the second embodiment of posterior cervical system 210 may be used as follows. Initially an incision is made over a facet joint 306 to be stabilized on one lateral side of the spine. Tissue is retracted to expose the spinal segment adjacent the facet joint, such as facet joint 306, to be stabilized. Using fluoroscopy, a trajectory 308 along the path of the facet joint is established, as depicted in FIG. 11B. Typically, the superior facet will be surgically addressed initially. Several sizes of tubular facet locks 212 having different diameters of lumen 212e may be provided in a surgical kit. This is so because the distance between the tapered wedge axis 222a and the lumen central axis 212f is fixed. A tubular facet lock 212 is selected that will have its central axis 212f align as closely as possible to the desired entry point 310 of superior lateral mass 302a. The selected tubular facet lock 212 is introduced into the surgical site along trajectory 308 and tapered wedge 222 is pressed into facet joint 306. An instrument 216 with drill 18 is then inserted through the lumen 212e of tubular facet lock 212 as depicted in FIG. 12B to form a pilot hole into the superior lateral mass 302a. In addition to stop 216d, instrument 116 may have bushings 216e on shaft 216a as shown in FIG. 12A, each having an outer diameter that provides relatively close sliding support for instrument 216 as it is introduced into tubular facet lock lumen 212e. Instrument 116 is then removed leaving tubular facet lock 212 in place with tapered wedge 222 remaining in facet joint 306.

Tubular guide 214 is then made ready for attachment to tubular facet lock 212 as shown in FIG. 12 C. Considering the anatomy of the patient, one of the dovetails 32, 34 or 36 of tubular guide 214 that will provide the closest proximity to the designated entry point 310 in inferior lateral mass 304a is chosen. Thus, the distance from the facet joint 306 to the desired entry point 310 of inferior lateral mass 304a may be adjusted. The selected dovetail projection, e.g. dovetail projection 34, is then slid into the dovetail recess 226 of facet lock 212 through the incision as shown in FIG. 12D. Instrument 216 with drill 18 is then inserted through lumen 14a of tubular guide 214 as shown in FIGS. 12C and 12D to form a pilot hole into the inferior lateral mass 304a. Instrument 116 is then removed from tubular guide 214 with both tubular facet lock 212 and tubular guide 214 remaining in place. Having formed appropriate pilot holes in the superior lateral mass 302a and the inferior lateral mass 304a, a respective lateral mass screw 118 is threaded into the each of the formed pilot holes as described above, with one lateral mass screw 118 introduced through tubular facet lock 212 and the other through tubular guide 214.

While the invention has been illustrated and described in detail in the drawings and foregoing description, the same should be considered as illustrative and not restrictive in character. For example, while attachment features 24 and 224 have been described herein as being constructed as dovetails, other attachment structures, such as cooperating cylindrical surfaces may also be used. As such, it is understood that only the preferred embodiments have been presented and that all changes, modifications and further applications that come within the spirit of the invention are desired to be protected.

What is claimed is:

1. A posterior cervical fixation system, comprising:
an elongate member having a distal end and a proximal end, said distal end including a tapered wedge projecting axially therefrom and defining a wedge axis, said tapered wedge being sized and configured for insertion into a facet joint of a cervical spine, said elongate member having an attachment feature; and
a tubular member having a distal end, a proximal end and a lumen extending therethrough along a central axis, said tubular member having a plurality of mating elements extending outwardly from said tubular member in a direction transverse to said central axis, each mating element terminating in an engagement surface that is spaced respectively at a different radial distance from said central axis, each mating element being sized and configured for individual releasable attachment to said attachment feature of said elongate member to selectively space said wedge axis and said central axis at different distances.

2. The posterior cervical fixation system of claim 1, wherein said elongate member is non-cannulated and has a solid cross-section.

3. The posterior cervical fixation system of claim 1, wherein said attachment feature comprises a dovetail recess with a base of said recess defining a support surface.

4. The posterior cervical fixation system of claim 3, wherein each of said mating elements comprises a dovetail projection configured to be matingly received in said dovetail recess of said attachment feature, the engagement surface of each mating element being selectively individually engageable with the support surface of said dovetail recess.

5. The posterior cervical fixation system of claim 4, wherein said plurality of mating elements comprises three dovetail projections.

6. The posterior cervical fixation system of claim 1, wherein said elongate member comprises a second attachment feature substantially opposite said attachment feature.

7. The posterior cervical fixation system of claim 1, wherein said elongate member is tubular and has a second lumen extending therethrough along a second central axis.

8. The posterior cervical fixation system of claim 1, wherein said tapered wedge has an outer surface that include serrations.

9. The posterior cervical fixation system of claim 1, wherein said attachment feature extends along a majority of the length of said elongate member.

10. The posterior cervical fixation system of claim 9, wherein each of said mating elements extends along a majority of the length of said tubular member.

11. The posterior cervical fixation system of claim 1, wherein each of said mating elements is tapered in the axial direction adjacent the distal end of said tubular member.

12. A posterior cervical fixation system, comprising:
a facet lock comprising an elongate member having a distal end and a proximal end, said distal end including a tapered wedge projecting axially therefrom and defining a wedge axis, said tapered wedge being sized and configured for insertion into a facet joint of a cervical spine, said elongate member including opposing first and second attachment features; and a tubular guide having a distal end, a proximal end and a lumen extending therethrough along a central axis, said tubular guide having a plurality of mating elements extending outwardly from said tubular guide in a direction transverse to said central axis, each mating element terminating in an engagement surface that is spaced respectively at a different radial distance from said central axis, each mating element being sized and configured for individual releasable attachment to one of said first or second attachment features of said elongate member to selectively space said wedge axis and said central axis at different distances.

13. The posterior cervical fixation system of claim 12, wherein each of said first and second attachment features comprises a dovetail recess with a base of each said recess defining a support surface, each support surface being spaced from said wedge axis at a fixed dimension, and wherein each of said mating elements comprises a dovetail projection configured to be matingly received in a respective dovetail recess of said first or second attachment features, the engagement surface of each mating element being selectively individually engageable with the support surface of one of said dovetail recesses of said first or second attachment features.

14. The posterior cervical fixation system of claim 13, wherein said lumen of said tubular guide is sized and configured to receive an instrument supporting a drill or tap for forming a pilot hole in a lateral mass of a cervical vertebral body.

15. The posterior cervical fixation system of claim 13, further including a screw placement tubular guide sized and configured for receiving and instrument supporting a lateral mass screw.

16. A posterior cervical fixation system, comprising:
a facet lock comprising an elongate tube having a distal end and a proximal end, said tube including a peripheral wall defining a first lumen extending therethrough along a first central axis, said elongate tube including a tapered wedge projecting axially from said peripheral wall at the distal end of said elongate tube, said tapered wedge defining a wedge axis, said wedge axis being substantially parallel to and offset from said first central axis, said tapered wedge being sized and configured for insertion into a facet joint of a cervical spine, said elongate tube including an attachment feature on an outer surface of said peripheral wall; and a tubular guide having a distal end, a proximal end and a second lumen extending therethrough along a central axis, said tubular guide having a plurality of mating elements extending outwardly from said tubular guide in a direction transverse to said central axis, each mating element terminating in an engagement surface that is spaced respectively at a different radial distance from said central axis, each mating element being sized and configured for individual releasable attachment to said attachment feature of said elongate member to selectively space said wedge axis and said central axis at different distances.

17. The posterior cervical fixation system of claim 16, wherein said tapered wedge and said attachment feature on said elongate tube are substantially axially aligned.

18. The posterior cervical fixation system of claim 16, wherein said first lumen is sized and configured to receive an instrument, supporting a drill, tap or a lateral mass screw.

19. The posterior cervical fixation system of claim 16, wherein said second lumen is sized and configured to receive an instrument, supporting a drill, tap or a lateral mass screw.

20. The posterior cervical fixation system of claim 19, further including a first lateral mass screw receivable through said first lumen, and a second lateral mass screw receivable through said second lumen.

* * * * *